United States Patent [19]

Trokel

[11] Patent Number: 5,711,762

[45] Date of Patent: Jan. 27, 1998

[54] LASER SURGERY APPARATUS AND METHOD

[75] Inventor: Stephen Trokel, New York, N.Y.

[73] Assignee: Visx, Incorporated, Sunnyvale, Calif.

[21] Appl. No.: 474,243

[22] Filed: Jun. 7, 1995

Related U.S. Application Data

[62] Division of Ser. No. 341,207, Dec. 5, 1994, which is a division of Ser. No. 893,841, Jun. 4, 1992, abandoned, which is a continuation of Ser. No. 673,541, Mar. 18, 1991, abandoned, which is a continuation of Ser. No. 109,812, Oct. 16, 1987, Pat. No. 5,108,388, which is a continuation of Ser. No. 859,212, May 2, 1986, abandoned, which is a continuation of Ser. No. 561,804, Dec. 15, 1983, abandoned.

[51] Int. Cl.$^6$ ............................................. A61N 5/03
[52] U.S. Cl. .................... 606/5; 606/2; 606/3; 606/16; 606/18
[58] Field of Search ............................................. 606/2–19

[56] References Cited

U.S. PATENT DOCUMENTS

| | | | |
|---|---|---|---|
| 3,330,182 | 7/1967 | Gerber et al. | |
| 3,710,798 | 1/1973 | Bredemeier | 128/395 |
| 3,769,963 | 11/1973 | Goldman et al. | 128/303.1 |
| 3,828,788 | 8/1974 | Karasov et al. | 606/4 |
| 3,982,541 | 9/1976 | L'Lsperance, Jr. | 606/4 |
| 4,170,997 | 10/1979 | Pinnon et al. | 433/114 |
| 4,301,118 | 11/1981 | Rosa et al. | 606/6 |
| 4,309,998 | 1/1982 | Aron noe rosa et al. | 128/303.1 |
| 4,409,979 | 10/1983 | Roussel et al. | 128/395 |
| 4,461,294 | 7/1984 | Baron | 606/5 |
| 4,485,499 | 12/1984 | Castlemann | 623/6 |
| 4,538,608 | 9/1985 | L'sperance, Jr. | 606/3 |
| 4,724,372 | 2/1988 | L'Esperance | 606/5 |
| 4,729,372 | 3/1988 | L'Esperance, Jr. | 606/5 |
| 4,732,148 | 3/1988 | L'Esperance | 606/5 |
| 4,744,360 | 5/1988 | Bath | 606/6 |
| 4,784,135 | 11/1988 | Blum et al. | 606/3 |
| 4,825,865 | 5/1989 | Zelman | 606/6 |
| 4,846,172 | 7/1989 | Berlin | 606/4 |

OTHER PUBLICATIONS

Facsimile letter dated Jun. 7, 1994 from Howard L. Milhench, attorney for VISX Corporation, to the European patent office containing applicant's preliminary response to an opposition by Summit Technology, Inc. to European patent application No. 86307420.9–2305/021842.

Paper in European patent application Nos. 86307420.9–2305/0218427 and 87306826.6–2302/0257836 titled "Affidavit of Stephen L. Trokel" Sworn on Dec. 5, 1995.

Form EPO 2042 dated Dec. 29, 1995 having reference No. J.17848 in European patent application No. 86307420.9–2302/0218427.

(List continued on next page.)

*Primary Examiner*—David M. Shay
*Attorney, Agent, or Firm*—Oblon, Spivak, McClelland, Maier & Neustadt, P.C.

[57] ABSTRACT

An argon-fluoride excimer laser or other laser source capable of generating far-ultraviolet radiation at 193 nm is pulsed with energy densities of greater than 20 mj per cm$^2$ at a repetition rate up to 25 pulses per second to direct its radiation through a mask and onto corneal tissue, or other biological matter, to form an ablation therein of predetermined configuration and depth by a process of ablative photodecomposition. The masks are formed with a slit, circular, crescent or other openings of widths between 30 and 800 microns, and may even be formed to provide a graded intensity center to edge. The mask is reflective or composed of or faced with an organic polymer to prevent heat build-up. Each micron of the depth of a 200 micron deep groove formed in corneal tissue, for example, resulted from the application of 1 joule per square centimeter of radiation, from a series of pulses delivered at intensities of between 100 mj and 200 mj per square centimeter, and at a laser pulse rate of between 1 and 25 Hertz, the entire groove taking 100 seconds.

23 Claims, 4 Drawing Sheets

OTHER PUBLICATIONS

Facsimile letter dated Feb. 8, 1995 from Howard L. Milhench, attorney for VISX Corporation, to the European patent office containing applicant's preliminary response to (1) an opposition by Firma Carl Zeiss and (2) an opposition by Summit Technology, Inc. to European patent application No. 87306826.6–2212/0257836.

Facsimile letter dated Jun. 2, 1994 from Howard L. Wibench, attorney for VISX Corporation, to the European patent office containing VISX's preliminary response to (1) an opposition by Firma Carl Zeiss and (2) an opposition by Summit Technology, Inc. to European patent application No. 87310283.4–0274205.

Letter dated Sep. 22, 1994 from Howard L. Milhench, attorney for VISX Corporation, to the European patent office containing applicant's preliminary response to (1) an opposition by Firma Carl Zeiss and (2) an opposition by Summit Technology, Inc. to European patent application No. 87310283.4–0274205.

Facsimile message dated Dec. 23, 1991 from Howard L. Milhench, attorney for VISX Corporation, to the European patent ofice containing VISX's observations regarding (1) an opposition by Synthelabo, Paris (FR) and (2) an opposition by Zeiss, Oberkochen (DE) to European patent application No. 896304315.4–2305.

Rebuttal Expert of Dr. Michael S. Feld Re: Validity; Civil Action No. 95–524–SLR; United States District Court for the District of Delaware; Dec. 30, 1996.

Report of James H. Brannon Pursuant to Federal rule of Civil Procedure 26; Civil Action No. 95–524 SLR; United States District Court for the District of Delaware, Dec. 9, 1996.

Rebuttal Expert Report of Dr. Jack Feinberg Re: Validity; Civil Action No. 95–524–SLR; United States District Court for the District of Delaware; Dec. 23, 1996.

Deposition of Alain Azema; Civil Action no. 95–524–SLR; United States District Court for the District of Delaware; Sep. 17, 1996.

Rebuttal Expert Report of Roger F. Steinert, M.D. Re: Validity; Civil Action No. 95–524–SLR; United States District Court for the District of Delaware; Dec. 30, 1996.

"Excimer Laser Surgery of the Cornea" by Trokel et al.; Am. J. Opthalmology; vol. 96; No. 6; Dec. 1983; pp. 710–715.

"Response to the Corneal Epithelium to KrF Excimer Laser Pulses" by Tabouda et al; Health Physics vol. 40, May 1981 pp. 677–683.

"An Extreem Sensitivity in the Corneal Epithelusa to For WARF Excime Laser Pulses" Toboda et al Aerospace Medical Assoc. 1981 Meeting San Antonio TX (Taboda et al (1981)).

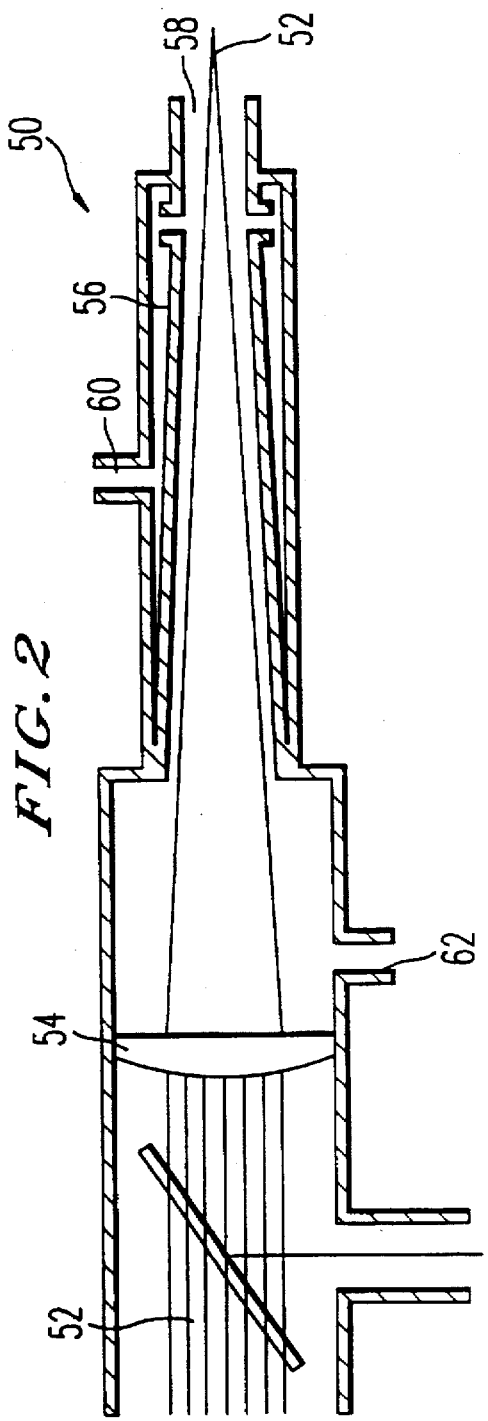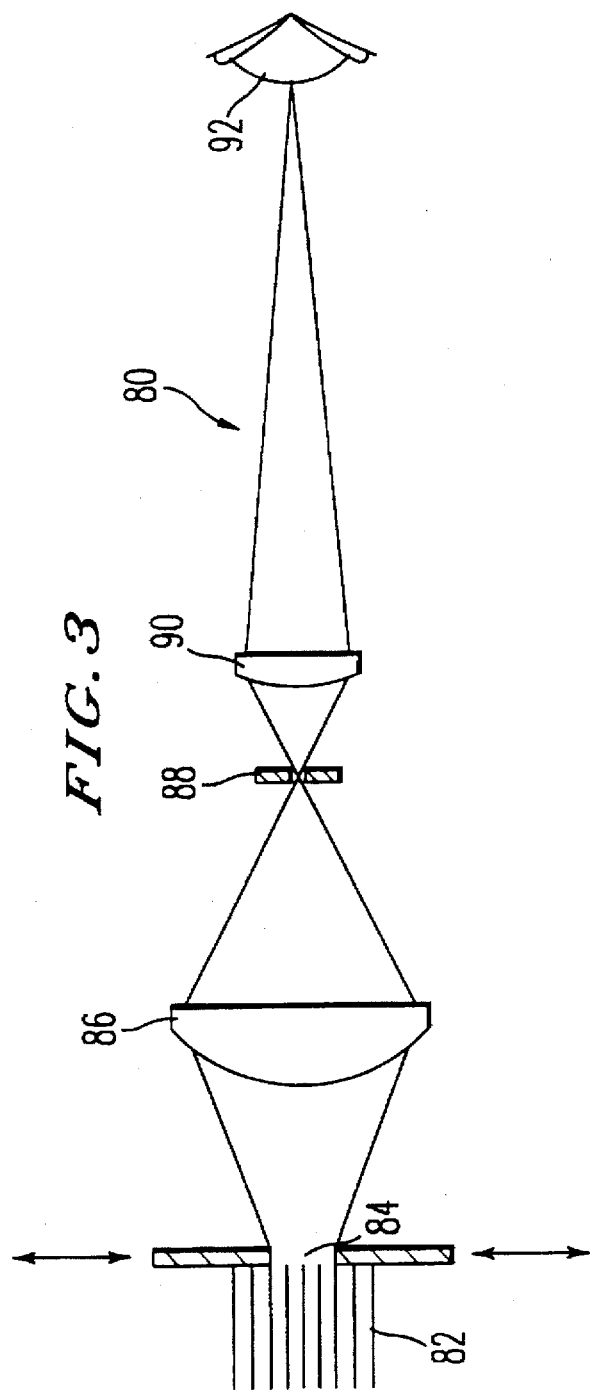

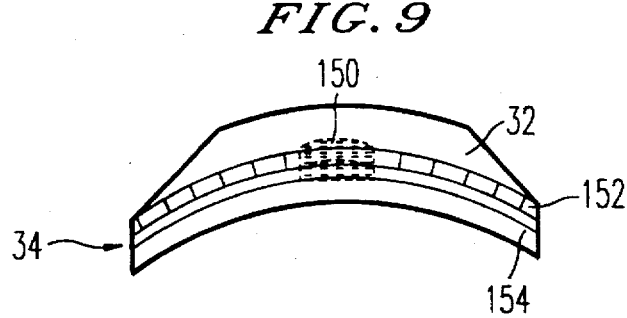
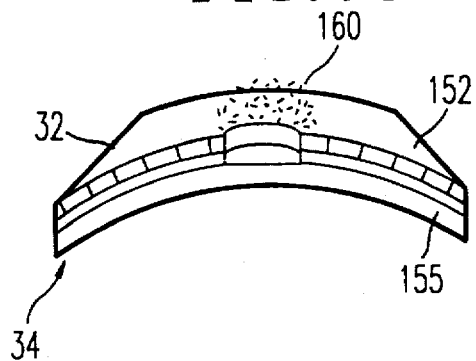
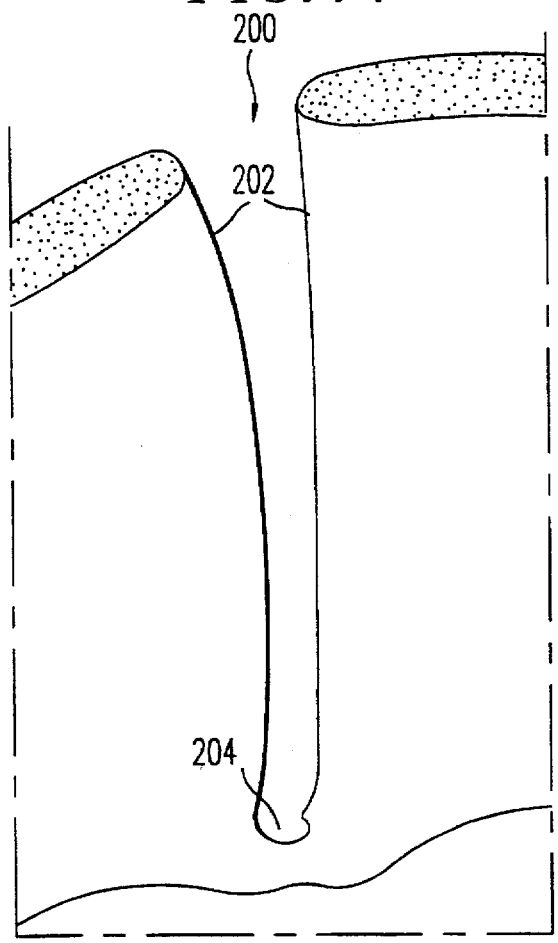
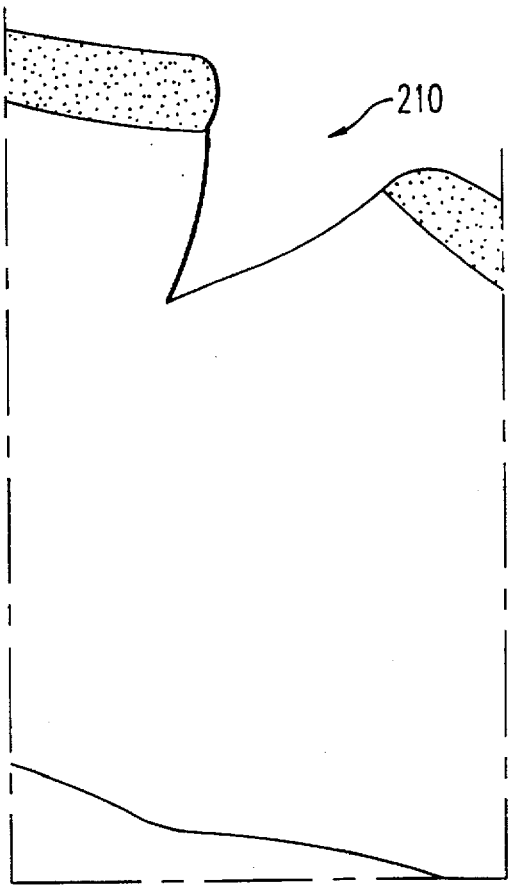

LASER SURGERY APPARATUS AND METHOD

This is a division of application Ser. No. 08/341,207 filed on Dec. 5, 1994, which is a division of application Ser. No. 07/893,841 filed on Jun. 4, 1992 abandoned, which is a continuation of application Ser. No. 07/673,541 filed on Mar. 18, 1991, now abandoned, which is a continuation of application Ser. No. 07/109,812 filed on Oct. 16, 1987, now U.S. Pat. No. 5,108,388, which is a continuation of application Ser. No. 06/859,212 filed on May 2, 1986 now abandoned, which is a continuation of application Ser. No. 06/561,804 filed on Dec. 15, 1983 abandoned.

BACKGROUND OF THE INVENTION

1. Field of Applications

This invention relates to surgical apparatus and methods; and more particularly to laser source surgical apparatus and methods.

2. Description of the Prior Art

Surgical procedures, especially surgical procedures wherein animal biological tissue, human biological tissue, or other matter are to be removed from a predetermined area and to a predetermined depth, require great surgical skill. In such procedures the skill of the surgeon is often enhanced by the use of apparatus particularly designed for surgical purposes. Such apparatus is more often than not very expensive, and in many instances requires complex procedures and a highly skilled or trained operator. Regardless of the expense of the apparatus, complexity of the procedure, or skill or training required to use the apparatus, it is often the availability of the apparatus that makes a particular surgical procedure possible. However, quite often the apparatus and associated surgical method, while facilitating a particular surgical procedure, produce unwanted effects on or to areas of the human or animal adjacent to those requiring the surgery.

Laser source apparatus has been utilized for surgical procedures, especially in ophthalmology. In such apparatus, a collimated beam of light, generated or produced by the laser source, is directed so as to focus on the area to be operated on. The light energy produced by the laser is converted to heat energy which, in turn, is utilized for the surgery. Such laser source facilitated surgical procedures are sometimes and may be otherwise referred to as thermal photocoagulation, as a fine controlled burn is produced. Other laser systems focus high powered pulses of light of sufficient intensity to produce optical (or dielectric) breakdown. This produces a surgical effect referred to as photo-disruption because the tissues are "disrupted" by the pulsar burn and associated shock wave.

Some available laser source apparatus for those surgical purposes, and associated surgical procedures, are described: in U.S. Pat. No. 3,982,541 granted on Sep. 28, 1976 to F. A. L'Esperance, Jr., for *Eye Surgical Instrument*; in U.S. Pat. No. 4,309,998 granted on Jan. 12, 1982 to D. S. Aron nee Rose et al for *Process And Apparatus For Ophthalmic Surgery*; in U.S. Pat. No. 4,336,809 granted on Jun. 29, 1982 to W. G. Clark for *Human And Animal Tissue Photoradiation System And Method*; and in U.S. Pat. No. 4,391,275 granted on Jul. 5, 1983 to F. Frankhauser, et al for *Method For the Surgical Treatment Of The Eye*.

However, utilization of such apparatus, more often than is desired, effects unwanted changes in adjacent remaining structures, causes thermal damage to areas adjacent the area requiring the surgical procedure, and results in undesirable irregular edges of the interaction site produced by the forces of optical breakdown. In addition, not every laser is suitable or acceptable if the surgeon is seeking the best possible results from the surgical procedures.

A new tissue interaction has been observed using pulsed ultraviolet light. A direct photochemical effect is observed which interacts exclusively with the irradiated tissues and produces no discernible effect upon the adjacent, unirradiated tissues. For lasers generating ultraviolet wavelengths shorter than 193 nm (nanometers), it has been found that optical delivery systems become extremely difficult to build because of the limited availability of refracting material. For lasers generating wavelengths longer than 200 nm, thermal effects become more dominant and the percentage of true ablative photodecomposition lessens.

Surgical procedures may be performed using pulsed ultraviolet light utilizing a mix of complete photoablation with some thermal effect as desired by the operating surgeon.

SUMMARY OF THE INVENTION

It is therefore an object of this invention to provide a new and improved laser source surgical apparatus.

It is another object of this invention to provide a new and improved method of laser surgery.

It is yet another object of this invention to provide a new and improved laser source apparatus for producing ablative photo-decomposition in ophthalmic surgery.

It is still another object of this invention to provide a new and improved method for surgery utilizing a far-ultraviolet laser source which produces ablative photodecomposition.

It is yet still another object of this invention to provide a new and improved laser source apparatus for ophthalmological surgery.

It is yet still another object of this invention to provide a new and improved method for laser source ophthalmological surgery.

It is a further object of this invention to provide a new and improved surgical apparatus utilizing a far-ultraviolet laser.

It is still a further object of this invention to provide a new and improved surgical method utilizing a far-ultraviolet argon-fluoride excimer laser.

This invention involves surgical apparatus and methods utilizing a laser generated light at particular wavelengths to effect ablative photodecomposition of particular areas of animal or human biological matter to a particular depth; and contemplates utilizing a laser producing far-ultraviolet radiation at a wavelength of 193 nm (nanometers) and directing the same to the particular area through a mask of predetermined configuration and in pulses of predetermined intensity for predetermined time periods so as to produce an opening of sharply defined edges and depth.

Other objects, features and advantages of the invention in its details of construction and arrangement of parts will be seen from the above, from the following description of the preferred embodiment when considered with the drawings and from the appended claims.

BRIEF DESCRIPTION OF THE DRAWINGS

In the drawings:

FIG. 2 is a schematic illustration of a laser delivery system for use with the apparatus and system of FIG. 1;

FIG. 3 is a schematic illustration of an ophthalmic delivery system for use with the apparatus and system of FIG. 1;

FIG. 9 is a sectional view through the schematic eye of FIG. 1 during the surgical procedure according to the instant invention, FIG. 10 is a sectional view through the schematic eye of FIGS. 1 and 9 following the surgical procedure according to the instant invention;

FIG. 11 is a sectional view perpendicular to a groove formed by photoablation according to the instant invention using the mask of FIG. 4; and FIG. 12 is a schematic view perpendicular to a V-shaped groove formed by photoablation according to the instant invention.

DESCRIPTION OF THE PREFERRED EMBODIMENT

For convenience, the invention will be described as applied to a laser photoablation and method utilizing an argon-fluoride excimer laser which generates far-ultraviolet radiation at 193 nm (nanometers) at predetermined pulse energy densities and repetition rates. Far-ultraviolet light may he produced by other lasers to be incorporated into this ophthalmic surgical system. Furthermore, the wavelengths of light applicable extend to 248 nm in spite of the less pure photodecomposition noted. The laser beam is thereafter directed through a mask formed from particular material and with one or more slit or circular openings to impinge upon an area of the cornea of an eye to form therein a groove of predetermined peripheral configuration and depth. It should be understood that without departing from the invention: the mask openings can be of any convenient peripheral configuration; the masks may be formed of any appropriate material; a fiber-optic pipe and rod delivery system may be utilized without masks, and the apparatus and system may be utilized for procedures on other tissues and biological matter, such as dental caries, human skin, and the like.

Figure 1:
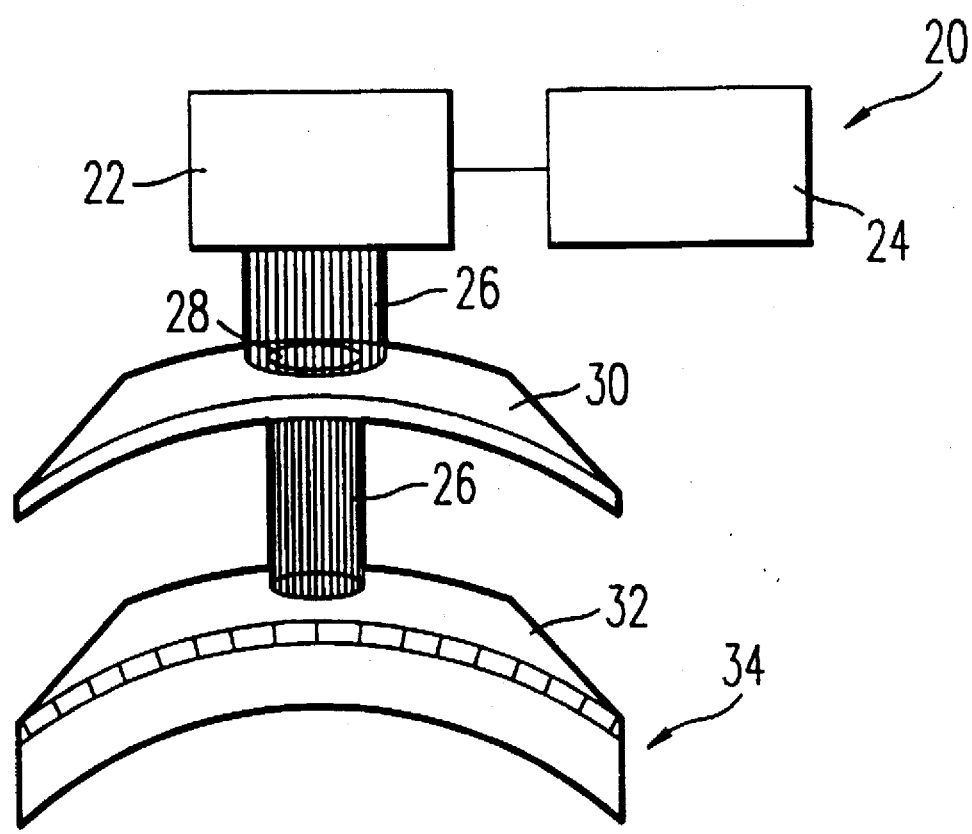
FIG. 1 is a schematic illustration of a photoablation apparatus and system incorporating the instant invention.

With reference to FIG. 1, there is generally shown at 20 a photoablation laser surgery apparatus and system utilizing a laser delivery system 22 and associated power supply and control system 24 by which a laser beam 26 is directed through openings 28 formed in a mask 30 and onto the cornea 32 of an eye 34, of either a human or an animal.

Laser delivery system 22 includes an argon-fluoride excimer laser such as one currently manufactured by Lamda Physik as their Model 201E. However, it is understood that other laser sources may be used to produce the effective ultraviolet light. Laser system 22 generates a laser beam 26 in the far-ultraviolet range of 193 nm (nanometers). Other ranges of ultraviolet wavelengths may be chosen. Power supply and control 24 is conventionally available and is interconnected to laser system 22 so that the output thereof is pulsed at pulse energy densities of greater than 420 mj per $cm^2$ (milijoules per square centimeter) at a repetition rate up to 25 pulses per second.

FIG. 2 illustrates a laser delivery system 50 wherein an ultra-violet laser beam 52 is directed through lens 54 and then through a passage 56 and opening 58. An appropriate opening 60 is provided to passage 56 for infusion of nitrogen or other similar gases. Another opening 62 is provided for passage 56 to provide a high vacuum therefor.

In FIG. 3, there is shown an ophthalmic delivery system 80 for generating and delivering a laser generated ultraviolet laser beam 82 through a variable slit 84 to and through a lens 86, through an aperture 88, through another lens 90, and onto an area, such as an eye 92, upon which a surgical procedure is to be performed.

Figure 4:
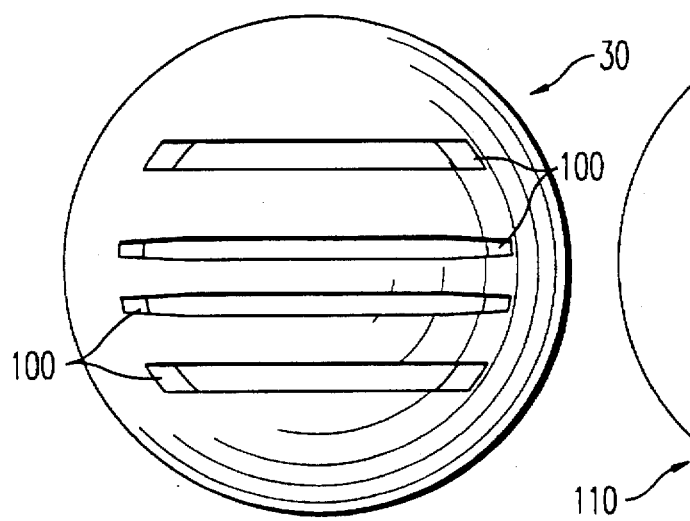
FIG. 4 is a plan view of a mask usable with the apparatus and system of FIG. 1.
Figure 5:
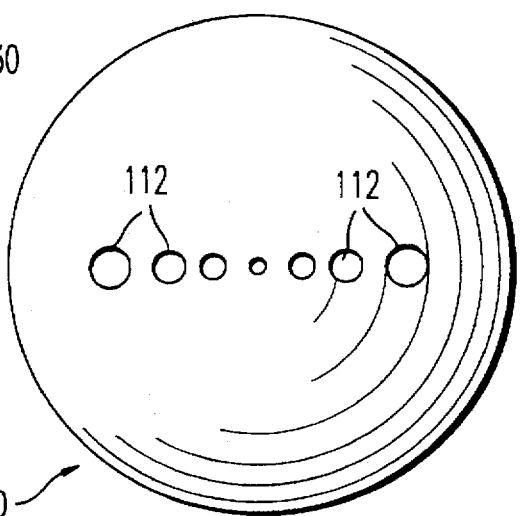
FIG. 5 is a plan view of another mask useable with the apparatus and system of FIG. 1.

Mask 30 (FIGS. 1 and 4) is formed from aluminum, or other appropriate material, and includes a number of slits 100 formed therethrough. The slits 100 range in width from 150 to 800 microns. While four slits have been shown for mask 30, it should be understood that a lesser or greater number of slits can be provided for mask 30 and that the widths as well as the slit configuration can be appropriately selected. An alternate mask 110, shown in FIG. 5, is formed with seven holes 112 drilled or otherwise formed therethrough. Holes 112 range in diameter from 100 microns to 750 microns. It should be understood that openings of any desired configuration (crescents, concentric rings, etc.) may be formed through masks 30 and 110. In addition, the mask may also be formed to provide a graded intensity center to edge or edge to center. The mask may be clad or covered with plastic or other polymers to prevent heating of the mask. The organic material will prevent ultra-violet light from striking the mask and heating it directly. The cladding prevents heating by being ablated by the ultraviolet light which is being shielded from the eye.

Figure 6:
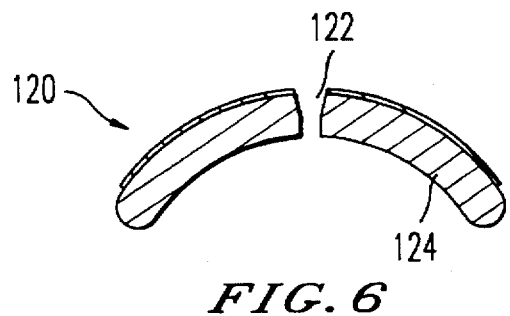
FIG. 6 is a sectional view through a mask useable with the apparatus and system of FIG. 1.

In FIG. 6, there is shown a mask 120 with an opening 122 and having a surface of 2000 Å chrome formed onto a base 124 of poly methyl methacrylate to reflect the ultra-violet light and to prevent heating. The mask is stabilized by a vacuum seal.

Figure 7:
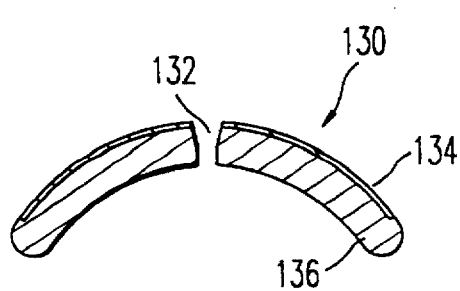
FIG. 7 is a sectional view of another mask usable with the apparatus and system of FIG. 1.

In FIG. 7, there is a mask 130 with an opening 132.

Figure 8:
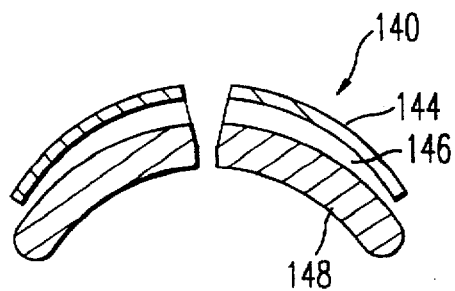
FIG. 8 is a sectional view of yet another mask usable with the apparatus and system of FIG. 1.

FIG. 8 shows still another alternate mask 140 with an opening 142. Mask 140 includes one or more metal cooling vanes 144 separated by an air space 146 from, but otherwise carried by or supported with respect to, a base 148 of stainless steel; all being stabilized by a vacuum seal.

While masks 120, 130, and 140 have been shown with single openings 122, 132, 142, respectively, it should by understood that any suitable number of openings may be formed in the masks, and that such openings may be formed with any appropriate configuration and width.

In use, laser apparatus 20 is positioned with respect to the area of tissue, biological matter, or the like upon which the surgical procedure is to be performed. In this instance, laser 20 is disposed with respect to cornea 32 of an eye 34 so that laser beam 26 will be directed towards mask 30 and then upon cornea 32. The output of laser 20 is delivered in a series of pulses under control of laser delivery system 22 and laser power supply and control system 24. For each micron depth of corneal tissue to be ablated, one joule per square centimeter was applied. Thus in forming a 200 micron deep groove, for example, 200 joules per $cm^2$ would be required. This was delivered in a series of pulses varying in intensity between 100 and 200 mj per square centimeter depending upon the area of the final focus of laser apparatus 20.

The laser pulse rate for apparatus 20 was between 1 and 25 Hertz and the pulses were delivered until sufficient total energy achieved the desired depth of cut. The maximum exposure time for the complete section of the cornea as described required 100 second (700 mj per $cm^2$). More rapid pulse rates create tissue heating distortion from gas pressure backup in the irradiated area. Higher energy densities in the irradiated area produce unwanted shock effects.

In FIG. 9, eye 34 is shown during the above described procedure and illustrates the bond breaking occurring at 150 in the epithelium 152 and stromal collagen 154. In FIG. 10, the ablated groove 160 is shown.

It should be noted that, by utilizing apparatus 20 and the described procedure, a groove 200 (FIG. 11) can be formed with parallel walls 202 and a square bottom 204.

Alternatively, a V-shaped groove 210 (FIG. 12) may be formed by apparatus 20 and the described procedure by directing laser beam 28 so that it strikes cornea 32 obliquely. By doing so, the energy distribution across a slit or other opening formed through mask 30 will cause the tissue to ablate more rapidly at one edge.

The described apparatus 20 and method causes a specific photo-chemical reaction and results in the ablation of corneal or other tissues without thermal damage to the adjacent remaining structures. The method allows incisions of controlled depth and shape. Defined volumes of tissue can be removed by masking to control the area ablating the tissue to a predetermined depth.

The corneal epithelium, for example, shows an extreme sensitivity to the 193 nm light emitted by the argon-fluoride excimer laser of apparatus 20. During the resulting ablative photodecomposition, the tissue is broken into smaller volatile fragments by direct photo-chemical interaction without heating the remaining adjacent tissues. Ultraviolet light at 193 nm is highly energetic, each photon having 6.4 electron volts. The high energy of each photon directly breaks intramolecular bonds.

Laser systems generating wavelengths larger than 193 nm thermally vaporize tissues with changes in adjacent remaining structures while laser systems generating wavelengths shorter than 193 nm are difficult to build because of the limited availability of refracting material. Tissues sectioned with a frequency double YAG laser run in a thermal mode show irregular edges of the interaction side produced by high tissue temperatures.

Apparatus 20 and the described method will produce an incision resembling that formed by a surgical cut. There will be a parallel between the gross corneal appearance and the mask, and no distortion of the stromal lamellae or epithelial edge. The groove walls will be parallel along their entire length and have a squared bottom.

The ablative photodecomposition accomplished by the described apparatus and method will provide grooves of a precisely determined shaped and to a precisely determined depth. This has the same clinical indication as lamellar keratectomy, since precise excision of the corneal tissue can be accomplished. In addition, a controlled penetrating corneal incision can, in principal, be done for corneal transplantation.

Radial incisions as well as concentric rings and crescents can be accomplished with the described apparatus and method. In fact, the laser light of the described method and apparatus can be applied to a circular mask of graded intensity center to edge. This would take away more tissue either centrally or peripherally depending on the distribution of light. The net effect would be either to steepen or flatten the cornea. The ability to make controlled radial incisions, or to selectively shape the corneal surface, allows modification of the refractive status of the eye.

As a further modification, apparatus 20 can be provided with a fiber-optic pipe or rod delivery system to allow placement of UV laser light to intraocular structures. This would allow (a) controlled filtering operation for glaucoma to be done subconjunctivally or via the anterior chamber; and (b) a "phakoemulsification" to be done with pulsed ultraviolet light rather than a vibrating titanium rod; (c) placement of the unit in the eye to section vitreous membranes as an alternative to rotating or oscillating knives.

Additionally, such a fiber-optic rod delivery system can be used in the treatment of dental caries by directing the light to the affected area or can be used in the removal of skin lesions As various possible embodiments might be made of the above invention, and as various changes might be made in the embodiments above set forth, it is to be understood that all matter herein described or shown in the accompanying drawings is to be interpreted as illustrative and not in a limiting sense. Thus, it will be understood by those skilled in the art, although preferred and alternative embodiments have been shown and described in accordance with the Patent Statutes, the invention is not limited thereto or thereby, since the embodiments of the invention particularly disclosed and described hereinabove are presented merely as an example of the invention. Other embodiments, forms, and modifications of the invention, coming within the proper scope and spirit of the appended claims, will of course readily suggest themselves to those skilled in the art. Thus, while there has been described what is at present considered to be the preferred embodiments of this invention, it will be obvious to those skilled in the art that various changes and modifications may be made therein, without departing from the invention, and it is, therefore, aimed in the appended claims to cover all such changes and modifications as fall within the true spirit and scope of the invention, and it is understood, although I have shown the preferred form of my invention, various modifications may be made in the details thereof, without departing from the spirit as comprehended by the following claims.

What is claimed is:

1. A system for use in a laser source surgical method for removing corneal tissue, said system comprising:

(a) a laser that produces a beam of radiation at a wavelength of about 193 nanometers in a series of pulses;

(b) a laser delivery system means for receiving said radiation from said laser and delivering a fraction of said radiation to a cornea; and (c) wherein said radiation produces a depth of ablation of approximately 1 micron for each accumulation of one joule per square centimeter of energy applied.

2. A system according to claim 1, wherein said laser delivery system means comprises a mask that has at least one radial aperture for producing radial corneal incisions.

3. A system according to claim 1, wherein said laser delivery system means comprises a mask that has optical apertures for producing ablations in the form of concentric rings.

4. A system according to claim 1, wherein said laser delivery system means comprises a mask for providing a graded intensity to the cornea with more intensity at the center than at the edge.

5. A system according to claim 1, wherein said laser delivery system means comprises a mask for providing a graded intensity to the cornea with more intensity at the edge than at the center.

6. A system according to claim 1, wherein said laser delivery system means comprises a mask for grading energy delivered to the cornea in each pulse from either center to edge or from edge to center, whereby an intensity delivered to the cornea is either greater at the center than at the edge or is greater at the edge than at the center.

7. A system according to claim 1, which can produce pulses at said cornea which have between 100 and 200 millijoules of energy per square centimeter.

8. A system according to claim 1, which can produce pulses at a rate of between 1 and 20 Hertz.

9. A system according to claim 1, which can grade energy delivered to the cornea in each pulse either center to edge or edge to center, whereby the intensity delivered to the cornea is either greater at the center than at the edge or is greater at the edge than at the center.

10. A system according to claim 1, further comprising means, including a mask, for controlling a volume of corneal tissue removed by said system during corneal laser surgery.

11. A system according to claim 1, wherein said beam of radiation has a wavelength of 193 nanometers.

12. A system according to claim 1, wherein said laser delivery system means comprises means for selectively shaping a surface of the cornea.

13. A system according to claim 1, wherein said laser delivery system means comprises means for removing corneal tissue from a central surface area of the cornea.

14. A system according to claim 1 wherein said laser includes means for delivering energy in a range of 100 to 200 millijoules per square centimeter per pulse.

15. A system according to claim 14, wherein said laser includes means for delivering the pulses at a rate of from 1 Hertz to 25 Hertz.

16. A system according to claim 1, wherein said laser delivery system means comprises a mask and said mask comprises an ablatable material.

17. A system according to claim 16, wherein said abatable material is a polymer.

18. A system according to claim 1, wherein said laser delivery system means comprises a mask and said mask comprises a base and at least one cooling vane spaced from said base by an air space and connected to said base.

19. A system according to claim 18, wherein said at least one cooling vane comprises metal.

20. A system according to claim 1, wherein said laser delivery system means comprises a mask and said mask comprises a plurality of cooling vanes.

21. A system according to claim 20, wherein said plurality of cooling vanes comprise metal.

22. A system according to claim 1, wherein said laser delivery system means comprises a mask and said mask comprises plastic.

23. A system according to claim 22, wherein said plastic is poly methyl methacrylate.

\* \* \* \* \*

UNITED STATES PATENT AND TRADEMARK OFFICE
CERTIFICATE OF CORRECTION

PATENT NO. : 5,711,762
DATED : JANUARY 27, 1998
INVENTOR(S) : STEPHEN TROKEL

It is certified that error appears in the above-identified patent and that said Letters Patent is hereby corrected as shown below:

```
Title page, item [56]
     line 7, change "L'Lsperance, Jr." to --L'Esperance, Jr.--;
     line 8, change "Pinnon et al." to --Pinnow et al.--;
     line 9, delete line 9 in its entirety;
     line 10, change "Aron noe rosa et al." to --Aron nee Rosa et al.--;
     line 14, change "L'sperance, Jr." to --L'Esperance, Jr.--;

Title page, item [73]
     line 4, change "Sunnyvale," to -- Santa Clara--;

Title page, under the heading OTHER PUBLICATIONS:
     line 3, change "VISX Corporation," to --VISX, Incorporated.

Title page, page 2,
     line 3, change "VISX Corporation," to --VISX Incorporated--;
     line 7, change "No. 87306826.6-2212/0257836." to --86304097.8(247260).--
     line 9, change "Wibench" to --Milhench--;
     line 9, change "VISX Corporation," to --VISX Incorporated--;
     line 13, change "87310283.4-0274205." to --87306826.6-2212/0257836.--
     line 15, change "VISX Corporation," to --VISX Incorporated--;
     line 21, change "VISX Corporation, " to --VISX Incorporated--.
```

UNITED STATES PATENT AND TRADEMARK OFFICE
CERTIFICATE OF CORRECTION

PATENT NO. : 5,711,762
DATED : APRIL 27, 1998
INVENTOR(S) : STEPHEN TROKEL

It is certified that error appears in the above-identified patent and that said Letters Patent is hereby corrected as shown below:

Title page, page 2,
    line 1, after "Expert" insert --Report--;
    line 4, change "rule" to --Rule--;
    line 20, change "Tabouda et al." to --Taboada et al.--;
    line 22, change "Extreem" to --Extreme--;
    line 22, change "Epithelusa" to --Epithelium--;
    lines 22-23, change "For WARF Excime" to --Far UV ArF Excimer--;
    line 23, change "Toboda" to --Taboada--;
    line 24, change "Taboda" to --Taboada--.

Column 6, line 11, change "lesions" to "lesions."

Signed and Sealed this

Fifteenth Day of September, 1998

Attest:

BRUCE LEHMAN

*Attesting Officer*    *Commissioner of Patents and Trademarks*